United States Patent [19]

Noetzel et al.

[11] 3,966,849

[45] June 29, 1976

[54] BROMINE-CONTAINING CYCLIC PHOSPHONIC ACID ESTERS

[75] Inventors: Siegfried Noetzel, Kelkheim, Taunus; Horst Jastrow, Niederhochstadt, Taunus; Edgar Fischer, Frankfurt am Main, all of Germany

[73] Assignee: Hoechst Aktiengesellschaft, Frankfurt am Main, Germany

[22] Filed: Aug. 5, 1974

[21] Appl. No.: 494,877

[30] Foreign Application Priority Data
Aug. 7, 1973  Germany.............................. 2339863

[52] U.S. Cl. .............................. 260/937; 260/45.7 P
[51] Int. Cl.² ........................ C07F 9/15; C08K 5/53
[58] Field of Search .................................... 260/937

[56] References Cited
UNITED STATES PATENTS 3,033,887  5/1962  Wadsworth, Jr. et al........... 260/937
3,511,857  5/1970  Baranauckas et al........... 260/937 X

*Primary Examiner*—Anton H. Sutto
*Attorney, Agent, or Firm*—Curtis, Morris & Safford

[57] ABSTRACT

Bromine-containing phosphonic acid esters of the formula

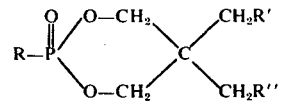

in which R represents a halogen-containing linear or branched aliphatic or cycloaliphatic hydrocarbon radical having from 1 to 8 carbon atoms and R' and R'' are hydrogen, halogen or alkyl groups having from 1 to 4 carbon atoms which may be closed to form a ring and/or substituted by halogen, at least one substituent being a bromine atom, are suitable as flame retardants for plastic materials, especially polystyrene and styrene copolymers.

5 Claims, No Drawings

BROMINE-CONTAINING CYCLIC PHOSPHONIC ACID ESTERS

The present invention relates to bromine-containing cyclic phosphonic acid esters suitable as flame-retardants in plastic materials.

It is known that readily inflammable plastic materials can be rendered flame resistant by the addition of halogen compounds. Flame resistant plastics are preferably used for the manufacture of porous thermoplastic materials, for example cellular plastics from styrene polymers.

Halogen compounds suitable for rendering plastics flame resistant are, for example, highly chlorinated non volatile hydrocarbons, which are preferably used in combination with antimony trioxide. It is rather disadvantageous that relatively high amounts of the chlorinated hydrocarbons are necessary, generally 15 to 20% by weight, calculated on the amount of plastic material, to obtain a satisfactory flameproofness. In the manufacture of foamed materials from expandable granular masses of a thermoplast the disadvantage is particularly great in that the high proportion of halogen compound detrimentally affects the welding of the granules. In many cases the foamed materials obtained have a poor mechanical strength.

It is also known that organic bromine compounds have a much better effect than the corresponding chlorine compounds. However, not all of the bromine compounds can be used as flame retardants. Suitable compounds are, for example, tetrabromobutane, dibromoethyl-benzene, dibromopropanol, tris(2,3-dibromopropyl)-phosphate, tetrabromocyclooctane and hexabromocyclo-dodecane. In general, the aforesaid compounds are used in an amount of from 5 to 10% by weight, calculated on the weight of plastic material.

A compound suitable for flame-proofing plastic materials should have the following properties: it should be difficultly volatile and odorless, it should not impair the mechanical properties of the plastic materials and exhibit a good effect when used in a small quantity. Moreover, it should not have a corrosive effect, it should be capable of being added to the monomers prior to polymerization without impeding the course of polymerization. To this effect it is necessary that the bromine compound is well soluble in the monomer to be polymerized, for example in styrene.

Organic bromine compounds known as flame retardants seldomly have all these properties to a sufficient extent. Partially they are volatile so that the flameproofness of the plastic materials treated therewith is lost after some time, partially they have a disgusting odor. Many known bromine compounds have a plasticizing effect. In the manufacture of foamed structures from expandable granules of thermoplasts flame-retarding agents having a plasticizing effect are unsuitable as they yield foamed structures of poor pressure resistance and dimensional stability. Finally, most organic bromine compounds impair the polymerization of monomeric polymerizable compounds. Consequently, they cannot be blended with the monomers, they have rather to be added to the finished polymers. Moreover, the solubility of the flame-retarding agents in the polymerizable monomers is mostly so low, that an addition during polymerization is unpracticable. There are many flame retardants that are soluble in the monomer to be polymerized, but, owing to the fact that they are incompatible with the polymer, they crystallize out in the polymer whereby the flame-proofness is diminished.

The present invention provides bromine-containing phosphonic acid esters of the formula

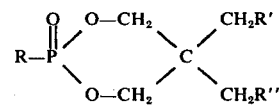

in which R represents a halogen-containing linear or branched aliphatic or cycloaliphatic hydrocarbon radical having from 1 to 8 carbon atoms and R' and R'' are hydrogen, halogen, or alkyl groups having from 1 to 4 carbon atoms which may be closed to form a ring and/or substituted by halogen, for example methyl, ethyl, n- and iso-propyl and n- and iso-butyl, at least one of the substituents being a bromine atoms.

It has also been found that thermoplastic materials have an excellent flame-proofness when they contain a phosphonic acid ester of the above formula in an amount such that the bromine content of the total mixture is in the range of from 0.3 to 20% by weight, preferably 0.8 to 10% by weight, calculated on the thermoplast.

The cyclic phosphonic acid esters in accordance with the invention have the advantage that they are well compatible with polymers such as polystyrene. As compared to brominated butadiene polymers, the phosphonic acid esters have the advantage that the same degree of flame-proofness can be obtained with a lower proportion thereof. Compared to the brominated phosphoric and phosphonic acid esters of the formula

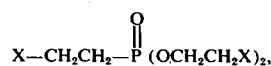

as disclosed, for example, in German Pat. No. 1,495,419 the cyclic phosphonic acid esters of the present invention have a much better stability to hydrolysis.

The phosphonic acid esters of the invention are readily accessible. They can be prepared by reacting at room temperature an unsaturated phosphonic acid dichloride in a solvent, for example 1,3-dioxane, with an alcohol of the formula

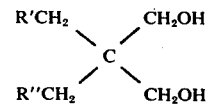

in the presence of a tertiary amine. For bromination elemental bromine is added on the carbon-carbon double bonds. For example, by reacting 1 mole of dibromoneopentyl glycol with 1 mole of vinyl-phosphonic acid chloride in the presence of 2 moles of triethyl amine in a dioxane solution the corresponding cyclic ester is obtained in a good yield. In chloroform the ester takes up at room temperature 2 equivalents bromine within several hours. A white crystalline product is obtained having a bromine content of 64.9% and a phosphorus content of 6.2%. In similar manner crystalline phosphonic acid esters containing 39.5% of bromine and 7.7% of phosphorus, or 47.6% of bromine and 9.5% of phosphorus, or 60% of bromine and 5.8% of phosphorus, respectively, can be prepared from vinylphosphonic acid dichloride and dichloro-neopentyl glycol, neopentyl glycol or 1,1-dimethylol-cyclohexene-3 as alcohol. The flame-retardant phosphonic acid esters of the invention are odorless, they have practically no vapor pressure and, hence, they are not volatile and are well compatible with a series of plastic materials, for example polystyrene. Flameresistant mixtures containing the flame-retarding compounds of the invention do not lose their flame-proofness even after a prolonged storage time.

The compounds of the invention can be used for flameproofing all readily inflammable plastic materials such as polymers and copolymers of ethylene, propylene, acrylonitrile, acrylic acid esters, methacrylic acid esters and vinyl acetate, as well as curable resins, for example unsaturated polyester resins, and polyaddition compounds such as polyurethanes. The compounds are especially suitable for flame-proofing styrene polymers such as polystyrene and copolymers of styrene and acrylonitrile or of styrene, butadiene-1,3 and acrylonitrile.

The flame-retardant mixtures can be prepared in various ways. Intimate mixtures of plastic material and flame retardant according to the invention can be prepared, for example, by blending the plastic material with the brominecontaining cyclic phosphonic acid ester in the heat at a temperature below 170°C in an extruder or a kneader. Both components can also be dissolved in a common solvent which is subsequently removed. An advantageous mode of operation is the polymerization of monomeric compounds in the presence of the flame-retarding compounds and peroxides decomposing at elevated temperature, for example di-tert.butyl peroxide, which acts as synergistic auxiliary. The compounds of the invention are especially favorable for the manufacture of flame resistant and expandable styrene polymers of small particle size by polymerization of styrene with readily volatile aliphatic hydrocarbons, advantageously in aqueous suspension. According to another method, instead of preparing intimate mixtures, the granular or spherical plastic mass is coated on the surface, for example in the case of expandable granular materials, especially styrene polymers of small particle size containing readily volatile hydrocarbons as blowing agent.

Further methods to prepare flame resistant mixtures with the compounds of the invention are illustrated in the following examples.

EXAMPLE 1

230 ml each of demineralized water and styrene were introduced into a 1 liter glass flask, heated to 90°C and a solution of 0.7% by weight of dibenzoyl peroxide, 0.12% by weight of t-butyl perbenzoate, 2.2 g of 1,2-dibromoethane-phosphonic acid dibromo-neopentyl glycol ester and 0.5 g of di-tert.butyl peroxide in 45 ml of styrene was added.

After having reached a conversion of 54% by weight of polystyrene, a solution of 1.7 g of polyvinyl alcohol (Elvanol$^{(R)}$5042) in 100 ml of water was added, whereupon a stable dispersion was obtained. Polymerization was carried out for 10 hours at 90°C and for 3 hours at 115°C. After separation of the aqueous phase the bead polymer was washed with water and isolated. The sheet made therewith was held for 30 seconds into a non luminous flame of a bunsen burner. After removal of the flame, the sheet extinguished at once, the extinguishing time was less than 1 second.

EXAMPLE 2

The polymerization was carried out as described in Example 1 with the exception that 2.8 g of 1,2-dibromoethanephosphonic acid dichloro-neopentyl glycol ester were used instead of 2.2 g of the dibromo-neopentyl glycol ester. A sheet made with the polymer obtained extinguished immediately after its removal from the non luminous flame of a bunsen burner. The extinguishing time was less than 1 second.

EXAMPLE 3

The polymerization was carried out as described in Example 1 with the exception that 2.6 g of 1,2-dibromoethane phosphonic acid neopentyl glycol ester were used instead of the dibromoneopentyl glycol ester. The sheet made with the polymer extinguished immediately after removal of the non luminous flame of a bunsen burner. The extinguishing time was less than 1 second.

EXAMPLE 4

The polymerization was carrid out as described in Example 1. 2.4 g of 1,2-dibromoethane-phosphonic acid ester of 1,1-dimethylol-3,4-dibromocyclohexane were used instead of the dibromo-neopentyl glycol ester of Example 1. The sheet made with the polymer extinguished immediately after removal of the non luminous flame of a bunsen burner, the extinguishing time was less than 1 second.

EXAMPLE 5

A 20% solution of polystyrene having a reduced specific viscosity of 1.4 in methylene chloride was prepared. 100 g of the solution were mixed while stirring with 0.2 g of 1,2-dibromoethane-phosphonic acid dibromo-neopentyl glycol ester and 0.05 g of di-tert.butyl peroxide. The mixture was poured into a dish (19 × 8 × 2 cm) of aluminium foil and kept for 12 hours under the hood. Thereafter, the aluminum foil was flattened and inserted into a polypropylene mould. After having covered the polystyrene plate with another aluminium foil the whole was placed in a perforated steel mould and plunged for 20 minutes in boiling water. The foamed sheet was dried under nitrogen for 12 hours at 70°C under a pressure of 400 mm Hg.

After 30 seconds flaming with a non luminous bunsen flame and subsequent removal of the flame, the sheet extinguished in less than 1 second.

What we claim is:

1. A phosphonic acid ester of the formula

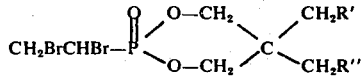

in which R' and R'' represent a member selected from the group consisting of hydrogen, chlorine, bromine and R' and R'' joined to form dibromo-cyclohexane.

2. The phosphonic acid ester of claim 1 wherein R' and R'' are bromine.

3. The phosphonic acid ester of claim 1 wherein R' and R'' are chlorine.

4. The phosphonic acid ester of claim 1 wherein R' and R'' are hydrogen.

5. The phosphonic acid ester of claim 1 wherein R' and R'' are joined and form 3,4-dibromo-cyclohexane.

* * * * *